(12) United States Patent
Lange et al.

(10) Patent No.: US 8,357,181 B2
(45) Date of Patent: Jan. 22, 2013

(54) INTERVERTEBRAL PROSTHETIC DEVICE FOR SPINAL STABILIZATION AND METHOD OF IMPLANTING SAME

(75) Inventors: Eric C. Lange, Collierville, TN (US); Jonathan Dewey, Memphis, TN (US); Kent M. Anderson, Memphis, TN (US); Thomas Carls, Memphis, TN (US); Fred J. Molz, IV, Collierville, TN (US); Matthew M. Morrison, Cordova, TN (US); Aurelien Bruneau, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1022 days.

(21) Appl. No.: 11/261,386

(22) Filed: Oct. 27, 2005

(65) Prior Publication Data

US 2007/0100340 A1    May 3, 2007

(51) Int. Cl.
*A61B 17/58* (2006.01)

(52) U.S. Cl. ................................. 606/248; 623/17.11

(58) Field of Classification Search ............ 606/61, 606/246, 248, 279; 623/16.11, 17.11, 17.15, 623/92, 105, 247, 249
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 3,997,138 A | 12/1976 | Crock et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,573,454 A | 3/1986 | Hoffman | |
| 4,604,995 A | 8/1986 | Stephens et al. | |
| 4,611,582 A | 9/1986 | Duff | |
| 4,657,550 A | 4/1987 | Daher | |
| 4,686,970 A | 8/1987 | Dove et al. | |
| 4,697,582 A | 10/1987 | William | |
| 4,743,260 A | 5/1988 | Burton | |
| 4,771,767 A | 9/1988 | Steffee | |
| 4,827,918 A | 5/1989 | Olerud | |
| 4,863,476 A | 9/1989 | Shepperd | |
| 4,887,596 A | 12/1989 | Sherman | |
| 4,931,055 A | 6/1990 | Bumpus et al. | |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

U.S. Appl. No. 11/095,215, filed Mar. 31, 2005, Anderson.

(Continued)

*Primary Examiner* — Alvin Stewart
*Assistant Examiner* — Tara Carter
(74) *Attorney, Agent, or Firm* — Sorell, Lenna & Schmidt, LLP (57) ABSTRACT

A prosthetic device and a method of implanting same between two vertebrae of a vertebral column to stabilize the column, according to which each vertebrae is engaged by a spacer, and the spacers are connected to permit relative movement between the spacers so that the distance between the spacers can vary to conform with the distance between the vertebrae and accommodate bending movements of the vertebral column.

3 Claims, 7 Drawing Sheets

U.S. PATENT DOCUMENTS

| | | | |
|---|---|---|---|
| 4,946,458 A | 8/1990 | Hams et al. | |
| 5,002,542 A | 3/1991 | Frigg | |
| 5,010,879 A * | 4/1991 | Moriya et al. | 606/276 |
| 5,011,484 A | 4/1991 | Breard | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,171,278 A | 12/1992 | Pisharodi | |
| 5,180,393 A | 1/1993 | Commarmond | |
| 5,201,734 A | 4/1993 | Cozad et al. | |
| 5,217,461 A | 6/1993 | Asher et al. | |
| 5,282,863 A | 2/1994 | Burton | |
| 5,306,275 A | 4/1994 | Bryan | |
| 5,306,308 A | 4/1994 | Gross et al. | |
| 5,330,472 A | 7/1994 | Metz-Stavenhagen | |
| 5,360,430 A | 11/1994 | Lin | |
| 5,366,455 A | 11/1994 | Dove | |
| 5,375,823 A | 12/1994 | Navas | |
| 5,383,454 A | 1/1995 | Bucholz | |
| 5,387,213 A | 2/1995 | Breard et al. | |
| 5,390,683 A | 2/1995 | Pisharodi | |
| 5,395,370 A | 3/1995 | Muller et al. | |
| 5,413,576 A | 5/1995 | Rivard | |
| 5,415,661 A | 5/1995 | Holmes | |
| 5,425,732 A | 6/1995 | Ulrich | |
| 5,437,672 A | 8/1995 | Alleyne | |
| 5,454,812 A | 10/1995 | Lin | |
| 5,456,722 A | 10/1995 | McLeod et al. | |
| 5,480,401 A | 1/1996 | Navas | |
| 5,496,318 A | 3/1996 | Howland | |
| 5,518,498 A | 5/1996 | Lindenberg et al. | |
| 5,527,314 A | 6/1996 | Brumfield et al. | |
| 5,540,688 A | 7/1996 | Navas | |
| 5,554,191 A | 9/1996 | Lahille et al. | |
| 5,562,660 A | 10/1996 | Grob | |
| 5,562,737 A | 10/1996 | Graf | |
| 5,575,819 A | 11/1996 | Amis | |
| 5,593,408 A | 1/1997 | Gayet et al. | |
| 5,609,634 A | 3/1997 | Voydeville | |
| 5,609,635 A | 3/1997 | Michelson | |
| 5,628,756 A | 5/1997 | Barker, Jr. et al. | |
| 5,645,599 A | 7/1997 | Samani | |
| 5,653,763 A | 8/1997 | Errico et al. | |
| 5,665,122 A | 9/1997 | Kambin | |
| 5,672,175 A | 9/1997 | Martin | |
| 5,674,295 A | 10/1997 | Ray et al. | |
| 5,674,296 A | 10/1997 | Bryan et al. | |
| 5,676,702 A | 10/1997 | Ratron | |
| 5,690,649 A | 11/1997 | Li | |
| 5,702,455 A | 12/1997 | Saggar | |
| 5,704,936 A | 1/1998 | Mazel | |
| 5,707,390 A | 1/1998 | Bonutti | |
| 5,716,416 A | 2/1998 | Lin | |
| 5,733,284 A | 3/1998 | Martin | |
| 5,755,798 A | 5/1998 | Papavero et al. | |
| 5,800,547 A | 9/1998 | Schäfer et al. | |
| 5,810,815 A | 9/1998 | Morales | |
| 5,827,328 A | 10/1998 | Buttermann | |
| 5,836,948 A | 11/1998 | Zucherman | |
| 5,851,183 A | 12/1998 | Bucholz | |
| 5,860,977 A | 1/1999 | Zucherman et al. | |
| 5,865,846 A | 2/1999 | Bryan et al. | |
| 5,871,445 A | 2/1999 | Bucholz | |
| 5,891,034 A | 4/1999 | Bucholz | |
| RE36,221 E | 6/1999 | Breard et al. | |
| 5,919,196 A | 7/1999 | Bobic et al. | |
| 5,921,987 A | 7/1999 | Stone | |
| 5,951,553 A | 9/1999 | Betz et al. | |
| 5,961,516 A | 10/1999 | Graf | |
| 5,964,805 A | 10/1999 | Stone | |
| 5,976,186 A | 11/1999 | Bao et al. | |
| 6,004,322 A | 12/1999 | Bernstein | |
| 6,007,496 A | 12/1999 | Brannon | |
| D420,132 S | 2/2000 | Bucholz et al. | |
| 6,021,343 A | 2/2000 | Foley et al. | |
| 6,022,376 A | 2/2000 | Assell et al. | |
| D422,706 S | 4/2000 | Bucholz et al. | |
| 6,048,342 A | 4/2000 | Zucherman et al. | |
| 6,059,829 A | 5/2000 | Schläpfer et al. | |
| 6,063,090 A | 5/2000 | Schlapfer | |
| 6,068,630 A | 5/2000 | Zucherman et al. | |
| 6,099,528 A | 8/2000 | Saurat | |
| 6,102,912 A | 8/2000 | Cazin et al. | |
| 6,110,209 A | 8/2000 | Stone | |
| 6,113,637 A | 9/2000 | Gill et al. | |
| 6,113,638 A | 9/2000 | Williams et al. | |
| 6,118,845 A | 9/2000 | Simon et al. | |
| 6,126,689 A | 10/2000 | Brett | |
| 6,127,597 A | 10/2000 | Beyar et al. | |
| 6,132,464 A | 10/2000 | Martin | |
| 6,143,031 A | 11/2000 | Knothe et al. | |
| 6,143,032 A | 11/2000 | Schafer et al. | |
| 6,143,033 A | 11/2000 | Paul et al. | |
| 6,156,067 A | 12/2000 | Bryan et al. | |
| 6,167,145 A | 12/2000 | Foley et al. | |
| 6,179,873 B1 | 1/2001 | Zientek | |
| 6,190,395 B1 | 2/2001 | Williams | |
| 6,190,414 B1 | 2/2001 | Young | |
| 6,214,050 B1 | 4/2001 | Huene | |
| 6,224,631 B1 | 5/2001 | Kohrs | |
| 6,226,548 B1 | 5/2001 | Foley et al. | |
| 6,235,038 B1 | 5/2001 | Hunter et al. | |
| 6,236,875 B1 | 5/2001 | Bucholz et al. | |
| 6,241,730 B1 | 6/2001 | Alby | |
| 6,248,105 B1 | 6/2001 | Schlapfer et al. | |
| 6,253,210 B1 | 6/2001 | Smith et al. | |
| 6,267,764 B1 | 7/2001 | Elberg | |
| 6,277,149 B1 | 8/2001 | Boyle et al. | |
| 6,287,308 B1 | 9/2001 | Betz et al. | |
| 6,293,949 B1 | 9/2001 | Justis et al. | |
| 6,296,643 B1 | 10/2001 | Hopf et al. | |
| 6,299,613 B1 | 10/2001 | Ogilvie et al. | |
| 6,306,142 B1 | 10/2001 | Johanson et al. | |
| 6,325,805 B1 | 12/2001 | Ogilvie et al. | |
| 6,325,827 B1 | 12/2001 | Lin | |
| 6,340,363 B1 | 1/2002 | Bolger et al. | |
| 6,348,058 B1 | 2/2002 | Melkent et al. | |
| 6,352,537 B1 | 3/2002 | Strnad | |
| 6,364,883 B1 | 4/2002 | Santilli | |
| 6,371,957 B1 | 4/2002 | Amrein et al. | |
| 6,375,658 B1 | 4/2002 | Hangody et al. | |
| 6,375,682 B1 | 4/2002 | Fleischmann et al. | |
| 6,379,302 B1 | 4/2002 | Kessman et al. | |
| 6,381,485 B1 | 4/2002 | Hunter et al. | |
| 6,383,221 B1 | 5/2002 | Scarborough et al. | |
| 6,395,011 B1 | 5/2002 | Johanson et al. | |
| 6,402,750 B1 | 6/2002 | Atkinson et al. | |
| 6,402,756 B1 * | 6/2002 | Ralph et al. | 606/71 |
| 6,402,762 B2 | 6/2002 | Hunter et al. | |
| 6,419,704 B1 | 7/2002 | Ferree | |
| 6,434,415 B1 | 8/2002 | Foley et al. | |
| 6,434,507 B1 | 8/2002 | Clayton et al. | |
| 6,436,099 B1 | 8/2002 | Drewry et al. | |
| 6,440,141 B1 | 8/2002 | Philippon | |
| 6,440,169 B1 | 8/2002 | Elberg et al. | |
| 6,451,019 B1 * | 9/2002 | Zucherman et al. | 606/249 |
| 6,470,207 B1 | 10/2002 | Simon et al. | |
| 6,474,341 B1 | 11/2002 | Hunter et al. | |
| 6,478,822 B1 | 11/2002 | Leroux et al. | |
| 6,488,033 B1 | 12/2002 | Cerundolo | |
| 6,488,682 B2 | 12/2002 | Kikuchi et al. | |
| 6,488,683 B2 | 12/2002 | Lieberman et al. | |
| 6,490,467 B1 | 12/2002 | Bucholz et al. | |
| 6,491,699 B1 | 12/2002 | Henderson et al. | |
| 6,503,279 B1 | 1/2003 | Webb et al. | |
| 6,520,963 B1 | 2/2003 | McKinley | |
| 6,520,991 B2 | 2/2003 | Huene | |
| 6,530,955 B2 | 3/2003 | Boyle et al. | |
| 6,535,756 B1 | 3/2003 | Simon et al. | |
| 6,540,668 B1 | 4/2003 | Schulz et al. | |
| 6,540,785 B1 | 4/2003 | Gill et al. | |
| 6,547,823 B2 | 4/2003 | Scarborough et al. | |
| 6,551,320 B2 | 4/2003 | Lieberman et al. | |
| 6,553,152 B1 | 4/2003 | Miller et al. | |
| 6,554,831 B1 | 4/2003 | Rivard et al. | |
| 6,554,833 B2 | 4/2003 | Levy | |

| | | |
|---|---|---|
| 6,565,605 B2 | 5/2003 | Goble |
| 6,582,433 B2 | 6/2003 | Yun |
| 6,582,467 B1 | 6/2003 | Teitelbaum et al. |
| 6,592,588 B1 | 7/2003 | Bobic et al. |
| 6,613,090 B2 | 9/2003 | Fuss et al. |
| 6,616,669 B2 | 9/2003 | Ogilvie et al. |
| 6,620,196 B1 | 9/2003 | Trieu |
| 6,623,484 B2 | 9/2003 | Betz et al. |
| 6,626,904 B1 | 9/2003 | Jammet et al. |
| 6,626,944 B1 | 9/2003 | Taylor |
| 6,636,757 B1 | 10/2003 | Jascob et al. |
| 6,645,207 B2 | 11/2003 | Dixon et al. |
| 6,645,211 B2 | 11/2003 | Magana |
| 6,663,635 B2 | 12/2003 | Frigg et al. |
| 6,669,635 B2 | 12/2003 | Kessman et al. |
| 6,685,742 B1 | 2/2004 | Jackson |
| 6,695,842 B2 | 2/2004 | Zucherman et al. |
| 6,706,067 B2 | 3/2004 | Shimp et al. |
| 6,708,184 B2 | 3/2004 | Smith et al. |
| 6,709,435 B2 | 3/2004 | Lin |
| 6,723,126 B1 | 4/2004 | Berry |
| 6,725,080 B2 | 4/2004 | Melkent et al. |
| 6,730,092 B2 | 5/2004 | Songer |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,740,086 B2 | 5/2004 | Richelsoph |
| 6,740,118 B2 | 5/2004 | Eisermann et al. |
| 6,746,450 B1 | 6/2004 | Wall et al. |
| 6,749,614 B2 | 6/2004 | Teitelbaum et al. |
| 6,752,831 B2 | 6/2004 | Sybert et al. |
| 6,754,374 B1 | 6/2004 | Miller et al. |
| 6,758,863 B2 | 7/2004 | Estes et al. |
| 6,761,720 B1 | 7/2004 | Senegas |
| 6,767,354 B2 | 7/2004 | Johanson et al. |
| 6,773,437 B2 | 8/2004 | Ogilvie et al. |
| 6,783,527 B2 | 8/2004 | Drewry et al. |
| 6,796,988 B2 | 9/2004 | Melkent et al. |
| 6,835,205 B2 | 12/2004 | Atkinson et al. |
| 6,843,805 B2 | 1/2005 | Webb et al. |
| 6,852,114 B2 | 2/2005 | Cerundolo |
| 6,875,212 B2 | 4/2005 | Shaolian et al. |
| 6,892,090 B2 | 5/2005 | Verard et al. |
| 6,899,713 B2 | 5/2005 | Shaolian et al. |
| 6,905,512 B2 | 6/2005 | Paes et al. |
| 6,920,347 B2 | 7/2005 | Simon et al. |
| 6,932,820 B2 * | 8/2005 | Osman ............... 606/71 |
| 6,946,000 B2 | 9/2005 | Senegas et al. |
| 6,978,166 B2 | 12/2005 | Foley et al. |
| 6,981,975 B2 | 1/2006 | Michelson |
| 7,007,699 B2 | 3/2006 | Martinelli et al. |
| 7,008,427 B2 * | 3/2006 | Sevrain ............... 606/71 |
| 7,011,685 B2 | 3/2006 | Arnin et al. |
| 7,018,415 B1 * | 3/2006 | McKay ............ 623/17.15 |
| 7,041,136 B2 | 5/2006 | Goble et al. |
| 7,048,736 B2 | 5/2006 | Robinson et al. |
| RE39,133 E | 6/2006 | Clayton et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,186,254 B2 * | 3/2007 | Dinh et al. ............... 606/61 |
| 7,201,751 B2 * | 4/2007 | Zucherman et al. ........ 606/249 |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,442,208 B2 | 10/2008 | Mathieu et al. |
| 7,445,637 B2 | 11/2008 | Taylor |
| 2002/0029039 A1 * | 3/2002 | Zucherman et al. ............ 606/61 |
| 2002/0128716 A1 * | 9/2002 | Cohen et al. ............... 623/17.15 |
| 2002/0133155 A1 | 9/2002 | Ferree |
| 2002/0143329 A1 | 10/2002 | Serhan et al. |
| 2002/0143331 A1 | 10/2002 | Zucherman et al. |
| 2003/0009226 A1 | 1/2003 | Graf |
| 2003/0023241 A1 | 1/2003 | Drewry et al. |
| 2003/0055427 A1 | 3/2003 | Graf |
| 2003/0088251 A1 | 5/2003 | Braun et al. |
| 2003/0093078 A1 | 5/2003 | Ritland |
| 2003/0100897 A1 | 5/2003 | Metz-Stavenhagen |
| 2003/0109880 A1 | 6/2003 | Shirado et al. |
| 2003/0153915 A1 | 8/2003 | Nekozuka et al. |
| 2003/0171749 A1 | 9/2003 | Le Couédic et al. |
| 2003/0191470 A1 | 10/2003 | Ritland |
| 2003/0220642 A1 | 11/2003 | Freudiger |
| 2003/0220643 A1 | 11/2003 | Ferree |
| 2004/0002708 A1 | 1/2004 | Ritland |
| 2004/0034437 A1 | 2/2004 | Schmieding |
| 2004/0039400 A1 | 2/2004 | Schmieding et al. |
| 2004/0049189 A1 | 3/2004 | Le Coudic et al. |
| 2004/0059425 A1 | 3/2004 | Schmieding |
| 2004/0073215 A1 | 4/2004 | Carli |
| 2004/0082954 A1 | 4/2004 | Teitelbaum et al. |
| 2004/0092939 A1 * | 5/2004 | Freid et al. ............ 606/79 |
| 2004/0097931 A1 | 5/2004 | Mitchell |
| 2004/0116927 A1 | 6/2004 | Graf |
| 2004/0133204 A1 | 7/2004 | Davies |
| 2004/0138666 A1 | 7/2004 | Molz, IV et al. |
| 2004/0147928 A1 | 7/2004 | Landry et al. |
| 2004/0167625 A1 | 8/2004 | Beyar et al. |
| 2004/0172025 A1 | 9/2004 | Drewry et al. |
| 2004/0176771 A1 | 9/2004 | Schnieding |
| 2004/0193154 A1 | 9/2004 | Leatherbury et al. |
| 2004/0199255 A1 | 10/2004 | Mathieu et al. |
| 2004/0215341 A1 | 10/2004 | Sybert et al. |
| 2004/0220569 A1 | 11/2004 | Wall et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0038432 A1 | 2/2005 | Shaolian et al. |
| 2005/0049708 A1 | 3/2005 | Atkinson et al. |
| 2005/0065515 A1 | 3/2005 | Jahng |
| 2005/0065516 A1 | 3/2005 | Jahng |
| 2005/0085815 A1 | 4/2005 | Harms et al. |
| 2005/0090822 A1 | 4/2005 | DiPoto |
| 2005/0101962 A1 | 5/2005 | Schwenke et al. |
| 2005/0102028 A1 | 5/2005 | Arnin et al. |
| 2005/0124991 A1 | 6/2005 | Jahng |
| 2005/0125061 A1 | 6/2005 | Zucherman |
| 2005/0131405 A1 | 6/2005 | Molz, IV et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0154390 A1 | 7/2005 | Biedermann et al. |
| 2005/0154461 A1 | 7/2005 | Humphreys et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0165398 A1 | 7/2005 | Reiley |
| 2005/0171539 A1 | 8/2005 | Braun et al. |
| 2005/0171540 A1 | 8/2005 | Lim et al. |
| 2005/0171543 A1 | 8/2005 | Timm et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0182401 A1 | 8/2005 | Timm et al. |
| 2005/0182409 A1 | 8/2005 | Callahan et al. |
| 2005/0192581 A1 | 9/2005 | Molz et al. |
| 2005/0203511 A1 | 9/2005 | Wilson-MacDonald et al. |
| 2005/0203512 A1 | 9/2005 | Hawkins |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0203624 A1 | 9/2005 | Serhan et al. |
| 2005/0209694 A1 | 9/2005 | Loeb |
| 2005/0216004 A1 | 9/2005 | Schwab |
| 2005/0222569 A1 | 10/2005 | Panjabi |
| 2005/0222687 A1 | 10/2005 | Vunjak-Novakovic et al. |
| 2005/0228381 A1 | 10/2005 | Kirschman |

| | | | |
|---|---|---|---|
| 2005/0228391 A1 | 10/2005 | Levy et al. | |
| 2005/0240182 A1* | 10/2005 | Zucherman et al. ............ 606/61 | |
| 2005/0240183 A1 | 10/2005 | Vaughan | |
| 2005/0245929 A1 | 11/2005 | Winslow et al. | |
| 2005/0245930 A1 | 11/2005 | Timm et al. | |
| 2005/0261682 A1 | 11/2005 | Ferree | |
| 2005/0261685 A1 | 11/2005 | Fortin et al. | |
| 2005/0261686 A1 | 11/2005 | Paul | |
| 2005/0261768 A1 | 11/2005 | Trieu | |
| 2005/0267470 A1 | 12/2005 | McBride | |
| 2005/0267473 A1 | 12/2005 | Vaughan | |
| 2005/0277920 A1 | 12/2005 | Slivka et al. | |
| 2005/0277922 A1 | 12/2005 | Trieu et al. | |
| 2005/0277926 A1 | 12/2005 | Farris | |
| 2005/0277932 A1 | 12/2005 | Farris | |
| 2005/0288672 A1 | 12/2005 | Feree | |
| 2006/0004447 A1* | 1/2006 | Mastrorio et al. ......... 623/17.11 | |
| 2006/0004455 A1 | 1/2006 | Leonard et al. | |
| 2006/0015181 A1 | 1/2006 | Elberg | |
| 2006/0015183 A1* | 1/2006 | Gilbert et al. ............. 623/17.11 | |
| 2006/0060209 A1 | 3/2006 | Shepard | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0116690 A1 | 6/2006 | Pagano | |
| 2006/0122620 A1 | 6/2006 | Kim | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 | 10/2006 | Anderson | |
| 2006/0241757 A1 | 10/2006 | Anderson | |
| 2006/0264938 A1 | 11/2006 | Zucherman et al. | |
| 2006/0271044 A1 | 11/2006 | Petrini et al. | |
| 2006/0293662 A1* | 12/2006 | Boyer et al. ................... 606/61 | |
| 2007/0005064 A1 | 1/2007 | Anderson et al. | |
| 2007/0100340 A1 | 5/2007 | Lange et al. | |
| 2007/0123861 A1 | 5/2007 | Dewey et al. | |
| 2007/0129729 A1 | 6/2007 | Petit et al. | |
| 2007/0151116 A1 | 7/2007 | Malandain | |
| 2007/0167945 A1 | 7/2007 | Carls et al. | |
| 2007/0168038 A1 | 7/2007 | Trieu | |
| 2007/0168039 A1 | 7/2007 | Trieu | |
| 2007/0173820 A1 | 7/2007 | Trieu | |
| 2007/0173821 A1 | 7/2007 | Trieu | |
| 2007/0173823 A1 | 7/2007 | Dewey et al. | |
| 2007/0233068 A1 | 10/2007 | Bruneau et al. | |
| 2007/0233074 A1 | 10/2007 | Trieu et al. | |
| 2007/0250060 A1 | 10/2007 | Trieu et al. | |
| 2007/0282443 A1 | 12/2007 | Globerman et al. | |
| 2008/0027545 A1* | 1/2008 | Zucherman et al. ....... 623/17.11 | |
| 2008/0033553 A1* | 2/2008 | Zucherman et al. ....... 623/17.11 | |
| 2008/0033559 A1* | 2/2008 | Zucherman et al. ....... 623/17.16 | |
| 2008/0039947 A1* | 2/2008 | Zucherman et al. ....... 623/17.16 | |
| 2008/0065212 A1* | 3/2008 | Zucherman et al. ....... 623/17.11 | |
| 2008/0065213 A1* | 3/2008 | Zucherman et al. ....... 623/17.11 | |
| 2008/0065214 A1* | 3/2008 | Zucherman et al. ....... 623/17.11 | |
| 2008/0183210 A1* | 7/2008 | Zucherman et al. .......... 606/246 | |
| 2008/0221692 A1* | 9/2008 | Zucherman et al. ....... 623/17.16 | |

FOREIGN PATENT DOCUMENTS

| | | |
|---|---|---|
| DE | 4012622 | 7/1991 |
| DE | 4012622 C1 | 7/1991 |
| DE | 9112466 U1 | 1/1992 |
| EP | 0322334 B1 | 2/1992 |
| EP | 0689401 | 7/1995 |
| EP | 0667127 | 8/1995 |
| EP | 0669109 | 8/1995 |
| EP | 0677277 | 10/1995 |
| EP | 0820731 | 1/1998 |
| EP | 0767636 B1 | 1/1999 |
| EP | 1004276 A1 | 5/2000 |
| EP | 1138268 | 10/2001 |
| EP | 1138268 A1 | 10/2001 |
| EP | 1239785 B1 | 9/2002 |
| EP | 1281361 | 2/2003 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2735351 | 12/1996 |
| FR | 2774581 | 8/1999 |
| FR | 2775183 A1 | 8/1999 |
| FR | 2799948 | 4/2001 |
| FR | 2799949 | 4/2001 |
| FR | 2816197 A1 | 5/2002 |
| FR | 2851154 | 8/2004 |
| FR | 2858929 | 2/2005 |
| JP | 02-224660 | 9/1990 |
| JP | 09-075381 | 3/1997 |
| SU | 988281 | 1/1983 |
| SU | 1484348 | 7/1989 |
| WO | 92/01428 | 2/1992 |
| WO | 9424933 | 11/1994 |
| WO | WO 94/26192 | 11/1994 |
| WO | WO 94/26195 | 11/1994 |
| WO | 9519149 | 7/1995 |
| WO | 9611624 | 4/1996 |
| WO | 98/22050 | 5/1998 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | 02/051326 | 7/2002 |
| WO | 02051326 | 7/2002 |
| WO | 02102259 | 12/2002 |
| WO | 03003902 | 1/2003 |
| WO | 03015645 | 2/2003 |
| WO | WO 03/057055 A1 | 7/2003 |
| WO | 2004024010 | 3/2004 |
| WO | 2004/026188 | 4/2004 |
| WO | WO 2004/047689 A1 | 6/2004 |
| WO | WO 2004/047691 A1 | 6/2004 |
| WO | 2005/009300 | 2/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | 2005087121 | 9/2005 |
| WO | WO 2005/110258 A1 | 11/2005 |
| WO | 2005115261 | 12/2005 |
| WO | 2007001994 | 1/2007 |
| WO | WO 2007/034516 A1 | 3/2007 |
| WO | 2007052975 | 5/2007 |
| WO | 03003901 | 11/2007 |

OTHER PUBLICATIONS

U.S. Appl. No. 11/095,214, filed Mar. 31, 2005, Anderson.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertebral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébraces Lombaires, Gastambide, ed., 1995, pp. 122-132, Expansion Scientifique Française, Paris, France.

Senegas, "La Ligamentoplastie Inter Vertébrace Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une exparience clinique d'un implant postérieur amortissant," Rachis Revue de Pathologie Vertébrace, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

U.S. Appl. No. 11/508,349, filed Aug. 23, 2006 in the name of Bharadwaj.

U.S. Appl. No. 11/514,433, filed Sep. 9, 2006 in the name of Nycz et al.

U.S. Appl. No. 11/551,979, filed Oct. 23, 2006 in the name of Bharadwaj.
U.S. Appl. No. 11/409,639, filed Apr. 24, 2006 in the name of Anderson.
U.S. Appl. No. 11/417,382, filed May 4, 2006 in the name of Bruneau et al.
U.S. Appl. No. 11/438,763, filed May 23, 2006 in the name of Anderson et al.
U.S. Appl. No. 11/490,010, filed Jul. 20, 2006 in the name of Anderson et al.
U.S. Appl. No. 11/559,013, filed Nov. 13, 2006 in the name of Anderson et al.
U.S. Appl. No. 11/622,967, filed Jan. 12, 2007 in the name of Anderson.
Notification of Transmittal of the International Search Report and the Written Opinion of the International Searching Authority, or the Declaration dated Jul. 31, 2007 for corresponding PCT Application No. PCT/US2007/063281 (13 pages).
Notification of Transmittal of the International Search Report and the Written Opinion of the International Searching Authority, or the Declaration dated Aug. 2, 2007 for corresponding PCT Application No. PCT/US2007/062405 (9 pages).
Notification of Transmittal of the International Search Report and the Written Opinion of the International Searching Authority, or the Declaration dated Jul. 24, 2006 for corresponding PCT Application No. PCT/US2006/009173 (13 pages).
Notification of Transmittal of the International Search Report and the Written Opinion of the International Searching Authority, or the Declaration dated Nov. 15, 2006 for corresponding PCT Application No. PCT/US2006/023831 (14 pages).

* cited by examiner

INTERVERTEBRAL PROSTHETIC DEVICE FOR SPINAL STABILIZATION AND METHOD OF IMPLANTING SAME

BACKGROUND

The present invention relates to an intervertebral prosthetic device for stabilizing the human spine, and a method for implanting same.

Spinal discs that extend between adjacent vertebrae in vertebral columns of the human body provide critical support between the adjacent vertebrae. These discs can rupture, degenerate, and/or protrude by injury, degradation, disease, or the like to such a degree that the intervertebral space between adjacent vertebrae collapses as the disc loses at least a part of its support function, which can cause impingement of the nerve roots and severe pain.

In these cases, intervertebral prosthetic devices have been designed that can be implanted between the adjacent vertebrae, both anterior and posterior of the column, to prevent the collapse of the intervertebral space between the adjacent vertebrae and thus stabilize the spine.

However, many of these devices are relatively difficult to insert, and often do not provide an optimum fit with the anatomy.

SUMMARY

The intervertebral prosthetic device according to an embodiment of the invention overcomes the above deficiencies by providing improved biomechanics and increased strength, in addition to being relatively easy to insert, yet provides an improved fit with the anatomy.

Various embodiments of the invention may possess one or more of the above features and advantages, or provide one or more solutions to the above problems existing in the prior art.

DETAILED DESCRIPTION

Figure 1:
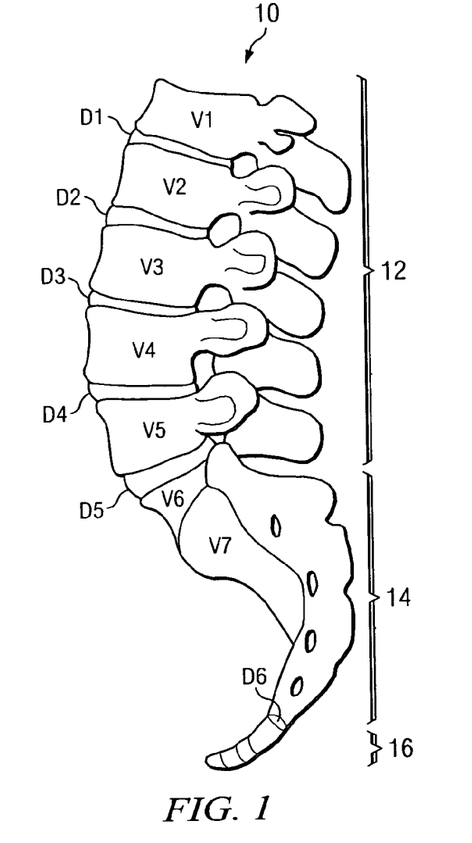
FIG. 1 is a side elevational view of an adult human vertebral column.
Figure 2:
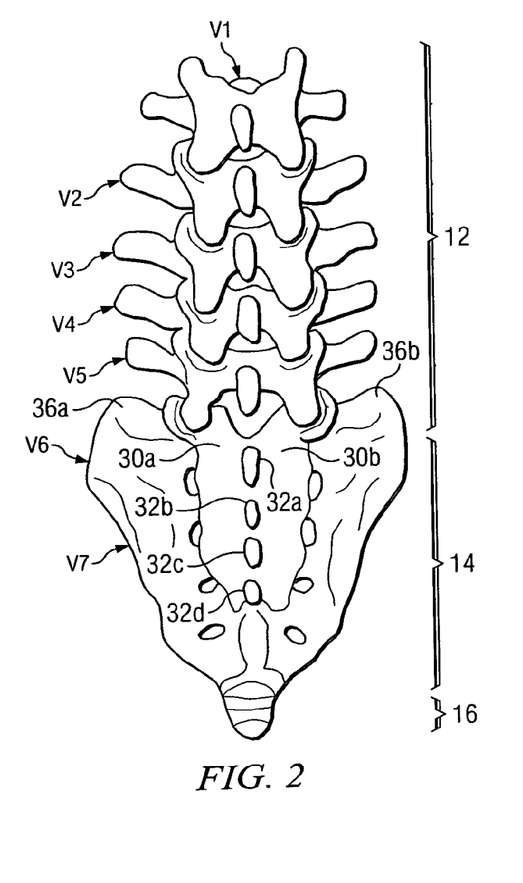
FIG. 2 is a posterior elevational view of the column of FIG. 1.

With reference to FIGS. 1 and 2, the reference numeral 10 refers, in general, to a human vertebral column 10. The lower portion of the vertebral column 10 is shown and includes the lumbar region 12, the vertebrae V6, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The vertebrae V6 includes five fused vertebrae, one of which is a superior vertebrae V6 separated from the vertebrae V5 by a disc D5. The other four fused vertebrae of the sacrum 14 are referred to collectively as V7. A disc D6 separates the vertebrae V6 from the coccyx 16 which includes four fused vertebrae (not referenced).

Figure 3:
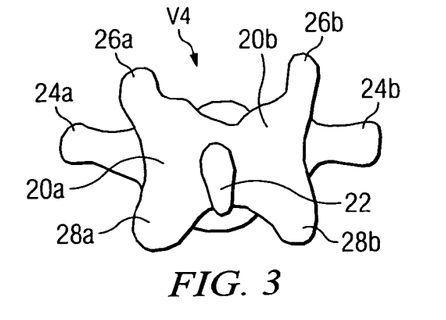
FIG. 3 is an enlarged, front elevational view of one of the vertebrae of the column of FIGS. 1 and 2

With reference to FIG. 3, the vertebrae V4 includes two laminae 20a and 20b extending to either side (as viewed in FIG. 2) of a spinous process 22 that extends posteriorly from the juncture of the two laminae. Two transverse processes 24a and 24b extend laterally from the laminae 20a and 20b, respectively. Two articular processes 26a and 26b extend superiorly from the laminae 20a and 20b respectively, and two articular processes 28a and 28b extend inferiorly from the laminae 20a and 20b, respectively. The inferior articular processes 28a and 28b rest in the superior articular process of the vertebra V5 to form a facet joint. Since the other vertebrae V1-V3 and V5 are similar to the vertebrae V4 they will not be described in detail.

Figure 4:
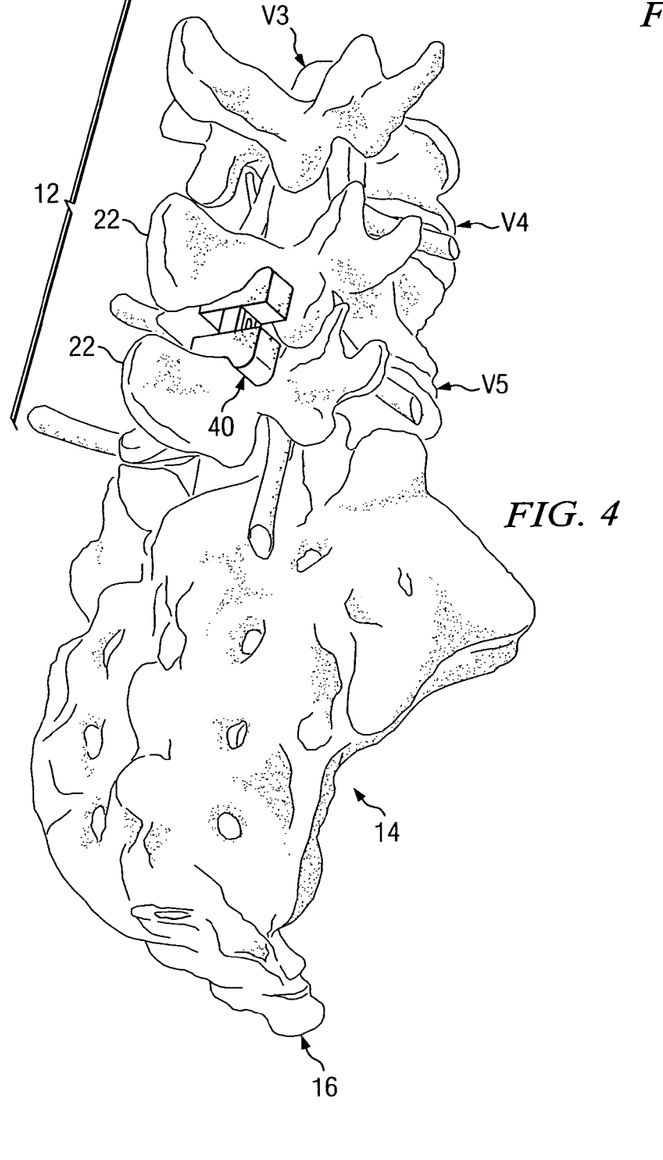
FIG. 4 is an enlarged, partial, isometric view of a portion of the column of FIGS. 1 and 2, depicting an intervertebral prosthetic device according to an embodiment of the invention inserted between two adjacent vertebrae.

Referring to FIG. 4, it will be assumed that, for one or more of the reasons set forth above, the vertebrae V4 and V5 are not being adequately supported by the disc D4 and that it is therefore necessary to provide supplemental support and stabilization of these vertebrae. To this end, an intervertebral prosthetic device 40 according to an embodiment of the invention is implanted between the spinous processes 22 of the vertebrae V4 and V5.

Figures 5, 6:
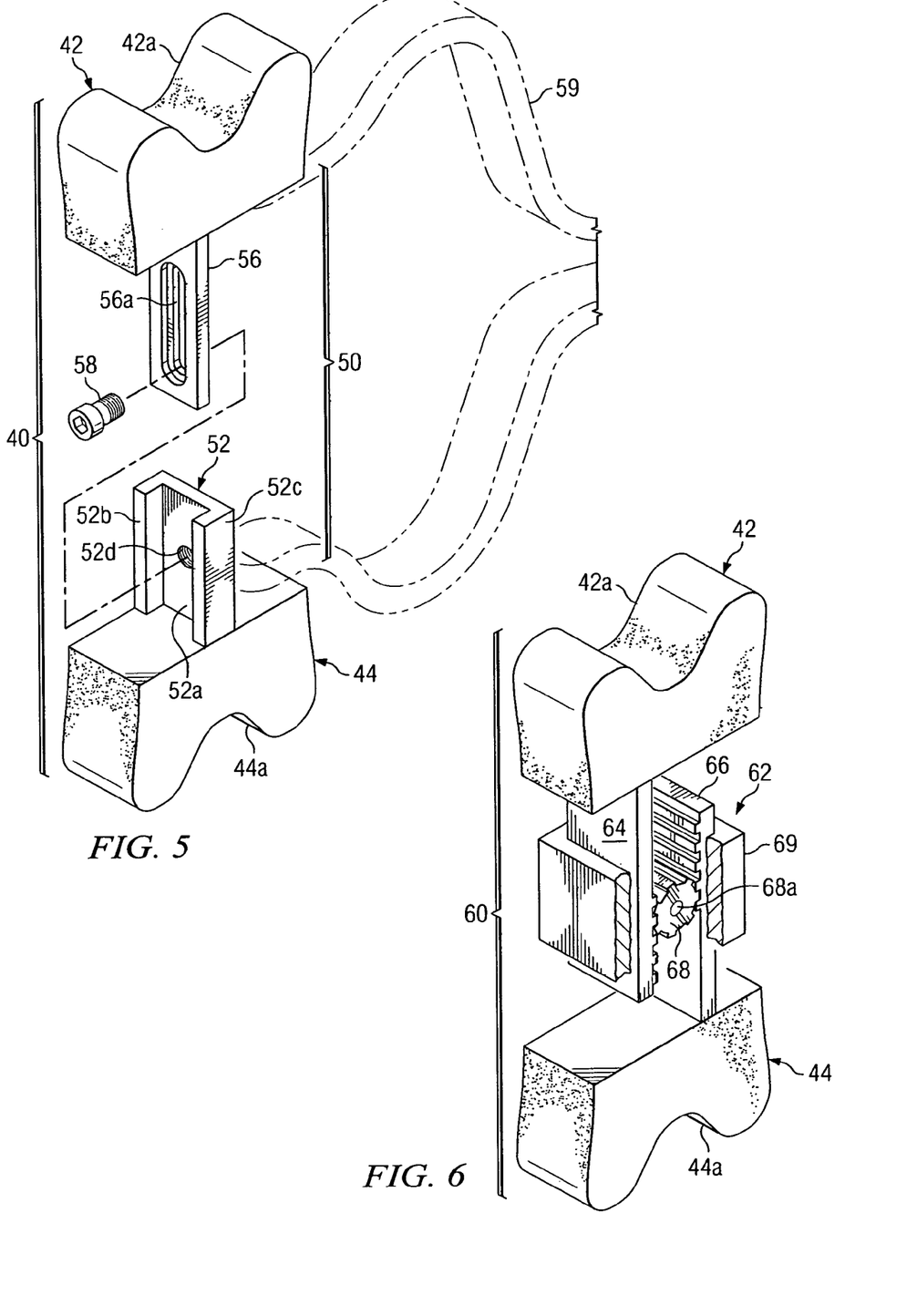
FIG. 5 is an enlarged, isometric, exploded view of the prosthetic device of FIG. 4.
FIGS. 6-8, an 9A-9C are views similar to that of FIG. 5, but depicting alternate embodiments.

The device 40 is shown in detail in FIG. 5 and includes a solid spacer 42 having a substantially rectangular cross-section with the exception that a longitudinal curved slot 42a is formed in one end portion. The slot 42a is sized so as to receive a process 22 of any of the vertebrae V1-V7, including the vertebrae V4 shown in FIG. 4. Another solid spacer 44 is provided that has a substantially rectangular cross-section with the exception that a longitudinal curved slot 44a is formed in one end portion. The slot 44a receives the process 22 (FIG. 4) from the vertebrae V5. Preferably, the spacers 42 and 44 are fabricated of a relative soft material.

An adjustable mechanism 50 connects the spacers 42 and 44 while permitting relative axial movement of the members relative to each other. The mechanism 50 consists of a bracket 52 extending from the end 44b of the spacer 44, and connected to the spacer in any conventional manner. The bracket 52 has a substantially U-shaped cross-section that includes a base 52a and two spaced, parallel, legs 52b and 52c extending from, and at right angles to, the base. An internally threaded opening 52d extends through the base 52a.

The mechanism 50 also includes a plate 56 extending from the end of the spacer 42 and connected to the spacer in any conventional manner. The plate 56 has a rectangular cross section and is sized so as to extend in the bracket 52, that is, in the area of the bracket 52 defined by the base 52a and the two legs 52b and 52c. An elongated slot 56a is formed through the plate 56.

A set screw 58 is provided that has an externally threaded shank portion that extends through the slot 56a in the plate 56 and threadedly engages the threaded opening 52d in the bracket 52. The screw 58 has a head portion the diameter of which is greater than the width of the slot 56a.

As an initial set-up prior to the surgical procedure, the plate 56 is positioned in the bracket 52, and the screw 58 is extended through the slot 56a and in threaded engagement with the opening 52d of the bracket 52. Then, the screw 58 is tightened only sufficiently to retain the plate 56 in the bracket 52 while permitting relative axial movement of the spacers 42 and 44, while the slot 56a defines the limits of the axial movement.

Referring to FIG. 4, the device 40 is inserted between the processes 22 of the vertebrae V4 and the vertebrae V5. The surgeon can then manually adjust the mechanism 50 (FIG. 5) and therefore the spacing between the spacers 42 and 44 intraoperatively in the manner discussed above, until the spinous processes 22 of the vertebrae V4 and V5 extend in the notches 42a and 44a, of the spacers 42 and 44, respectively, with an optimum fit. If needed, a conventional distractor 59, shown by the phantom lines in FIG. 5, can be used to assist in making the above adjustment, with the screw 88 tightened to the extent that it retains the spacers 42' and 44 in an extended position while permitting relative axial movement as necessary. When the optimum fit is achieved, the set screw 58 is tightened against the plate 56 to lock the plate to the bracket 52 and thus lock the spacers 42 and 44 in the desired position.

It can be appreciated that after the device 40 has been implanted in the manner discussed above, the device can respond to various movements of the patient that place stress on the vertebral column 10 (FIG. 1) and accommodate these movements by relative movement between the spacers 42 and 44. For example, if the patient bends backwardly, the spacers 42 and 44 would move closer together, and the set screw 58 permitting the relative axial movement. If the patient bends forwardly, then the axial spacing between the spacers 42 and 44 would increase, with the set screw 58 permitting the relative axial movement. In both of the above cases, when the patient returns to a normal position the set screw 58 would permit the spacers 42 and 44 to move back to their original position.

If the above backward movement is extreme, the spacers 42 and 44 could reach a position in which their corresponding ends abut. In this position, the end of the spacer 42 that abuts the corresponding end of the spacer 44 would compress slightly since the spacer 42 is fabricated of a relative soft material.

Thus, the device 40 is relatively easy to insert, provides an optimum fit between the processes of two adjacent vertebrae, and is adapted to vary in axial length in response to movements of the patient.

Referring to FIG. 6, another embodiment of an intervertebral prosthetic device is referred to, in general, by the reference numeral 60 and, is also adapted to be implanted between the spinous processes 22 of the vertebrae V4 and V5.

The device includes the same spacers 42 and 44 of the previous embodiment but utilizes a different connecting mechanism, which is referred to, in general, by the reference numeral 62.

The mechanism 62 includes a plate 64 extending from the end of the spacer 42 and connected to the spacer in any conventional manner, and a plate 66 extending from the end 44b of the spacer 44 and connected to the latter spacer in any conventional manner. The inner facing surfaces of the plates 64 and 66 are provided with teeth. A retainer 69 extends around the plates 64 and 66 and is partially shown in FIG. 6 in the interest of clarity.

A spur gear 68, having teeth formed on its outer surface, is mounted between the plates 64 and 66 and between the ends of the bracket. The teeth of the gear 68 are in engagement with the teeth of the plates 64 and 68 so that rotation of the gear causes translational movement of the plates relative to each other. Although not shown in the drawings it is understood that a conventional torsion spring can be attached to the gear 68 so that rotation of the gear in one direction cause the spring to coil up and tighten so that, when the rotation ceases the spring will uncoil and cause the gear to rotate in the other direction.

An opening 68a is provided in the gear 68 that receives a tool, such as an Allen wrench, or the like, to permit the gear to be manually rotated. To this end, and although not shown in the drawings, it is understood that an opening would be provided in one of the end plates of the bracket 69 that would register with a corresponding end of the gear 68 to permit access to the opening 68a gear for this purpose.

Referring to FIG. 4, the device 60 would be inserted between the processes 22 of the vertebrae V4 and the vertebrae V5 in the same manner as the device 40, as discussed above. The surgeon can then rotate the gear 68 to adjust the spacing between the spacers 42 and 44 until the spinous processes 22 of the vertebrae V4 and V5 extend in the notches 42a and 44a, of the spacers 42 and 44, respectively, with an optimum fit. If needed, the distractor 59, shown in the embodiment of FIG. 5, can be used to make the above adjustment.

It can be appreciated that after the device 60 has been implanted in the manner discussed above, the device can respond to various movements of the patient that place stress on the vertebral column 10 (FIG. 1) and accommodate these movements by relative movement between the spacers 42 and 44. For example, if the patient bends backwardly, the spacers 42 and 44 would move closer together, with the gear 68 and the above spring permitting the relative axial movement. If the patient bends forwardly, then the axial spacing between the spacers 42 and 44 would increase, with the gear 68 and the spring permitting the relative axial movement. In both of the above cases, when the patient returns to a normal position the spring would rotate the gear 68 in the manner discussed above to move the spacers 42 and 44 back to their original position.

If the above backward movement is extreme, the spacers 42 and 44 could reach a position in which their corresponding ends abut. In this position, the end of the spacer 42 that abuts the corresponding end of the spacer 44 would compress slightly since the spacer 42 is fabricated of a relative soft material.

Thus, the device 40 is relatively easy to insert, provides an optimum fit between the processes of two adjacent vertebrae, and is adapted to vary in axial length in response to movements of the patient.

As a result, the longitudinal, or axial, distance between the spacers 42 and 44 can be adjusted, depending on the distance between the processes 22 of the vertebrae V4 and V5. Thus, the device 60 is relatively easy to insert and provides an optimum fit between the two vertebrae V4 and V5. Thus, the above manual rotation of the gear 68 causes relative axial movement between the plates 64 and 66, and therefore the spacers 42 and 44. As a result, the longitudinal, or axial, distance between the spacers 42 and 44 can be adjusted, depending on the distance between the processes 22 of the vertebrae V4 and V5.

Figure 7:
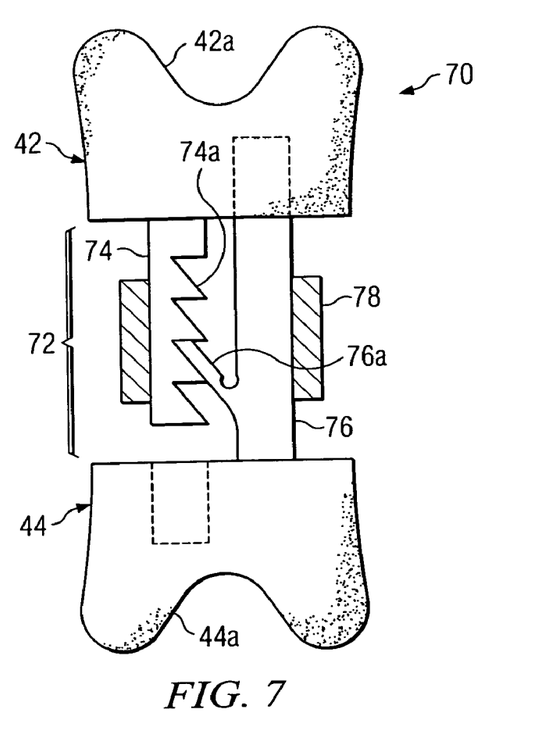

Another embodiment of an intervertebral prosthetic device is referred to, in general, by the reference numeral 70 in FIG. 7 and is also adapted to be implanted between the spinous processes 22 of the vertebrae V4 and V5.

The device 70 includes the same spacers 42 and 44 of the previous embodiment but utilizes a different connecting mechanism, which is referred to, in general, by the reference numeral 72.

The mechanism 72 includes a plate 74 extending downwardly from the end of the spacer 42, as viewed in the drawing, and connected to the spacer in any conventional manner.

A plate 76 extends upwardly from the end 44b of the spacer 44 and is connected to the latter spacer in any conventional manner.

The inner surface of the plate 74 is provided with a plurality of ratchet teeth 74a each of which has an angled surface extending downwardly from a horizontal surface. A flexible tab 76a is formed integrally with the plate 76 and projects outwardly from the inner surface of the plate 76. The length of the tab 76a is such that it can extend along the angled surface of a particular tooth 74a and abut the horizontal surface of a tooth immediately above the particular tooth. A retainer 78 extends around the plates 74 and 76 and is shown in cross section in the interest of clarity.

Thus, the plate 74, and therefore the spacer 42 can be moved manually in an upwardly direction relative to the plate 76, and therefore the spacer 44; and/or the plate 76, and therefore the spacer 44 can be moved in an downwardly direction relative to the plate 74, and therefore the spacer 42. During this movement, the tab 76a rides along the outer surfaces of the teeth 74a and, when the movement is stopped, the tab flexes outwardly to a position along the angled surface of a particular tooth.

The device 70 is inserted between the processes 22 of the vertebrae V4 and the vertebrae V5 in the same manner as the device 40, as shown in FIG. 4 and discussed above. The surgeon can then adjust the longitudinal spacing between the spacers 42 and 44 in the manner described above until the spinous processes 22 of the vertebrae V4 and V5 extend in the notches 42a and 44a, of the spacers 42 and 44, respectively, with an optimum fit. If needed, the distractor 59, shown in the embodiment of FIG. 5, can be used to assist in making the above insertion.

Figure 8:
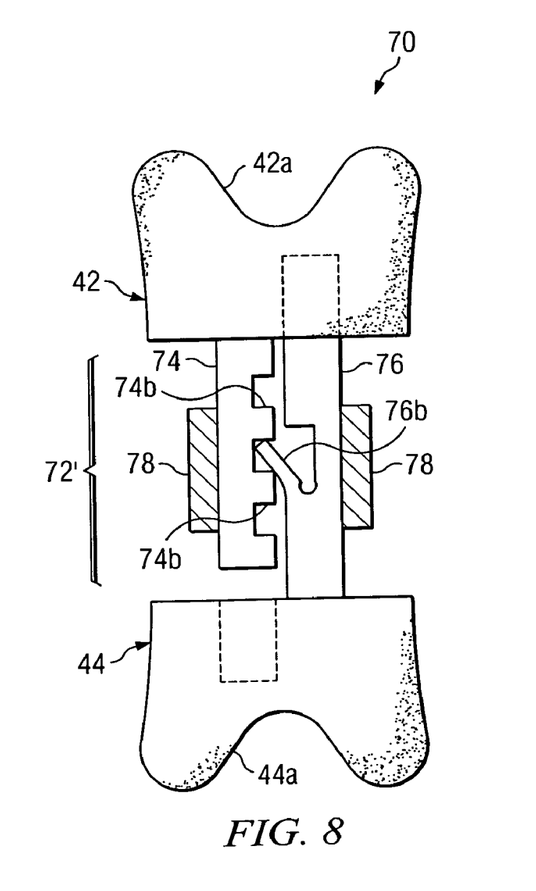

An alternate version of the mechanism 72 is shown by the reference numeral 72' in FIG. 8. The mechanism 72' is similar to the mechanism 72 of FIG. 7 and includes the plates 74 and 76 and the retainer 78. However the ratchet teeth 74a of the mechanism 72 are eliminated and the outer surface of the plate 74 of the mechanism 72' is provided with a plurality of axially-spaced indentations that form a plurality of axially-spaced teeth 74b having a rectangular cross-section.

A flexible tab 76b is bent out from a cut-out portion of the inner surface of the plate 76, with the length of the tab being such that it can ride along the teeth 74b when the plate 74 moves upwardly relative to the plate 76, and/or the plate 76 moves downwardly relative to the plate 74. When this movement is stopped, the tab 76b flexes into an indentation between adjacent teeth 74b to block any axial movement between the plate 74 downwardly relative to the plate 76, and/or movement of the plate 76 upwardly relative to the plate 74.

The device of FIG. 8 is inserted between the processes 22 of the vertebrae V4 and the vertebrae V5 and the axial distance between the spacers 42 and 44 is adjusted as described above, so that the spinous processes 22 of the vertebrae V4 and V5 extend in the notches 42a and 44a, of the spacers 42 and 44, respectively, with an optimum fit.

As a result, relative movement between the plates 74 and 76, and therefore the spacers 42 and 44, in a direction away from each other is permitted, while relative movement of the plates and the spacers in a direction towards each other is prevented.

Thus, the mechanism 72' of FIG. 8 enjoys the same advantages as the mechanism 72 of the FIG. 7.

Figure 9A:
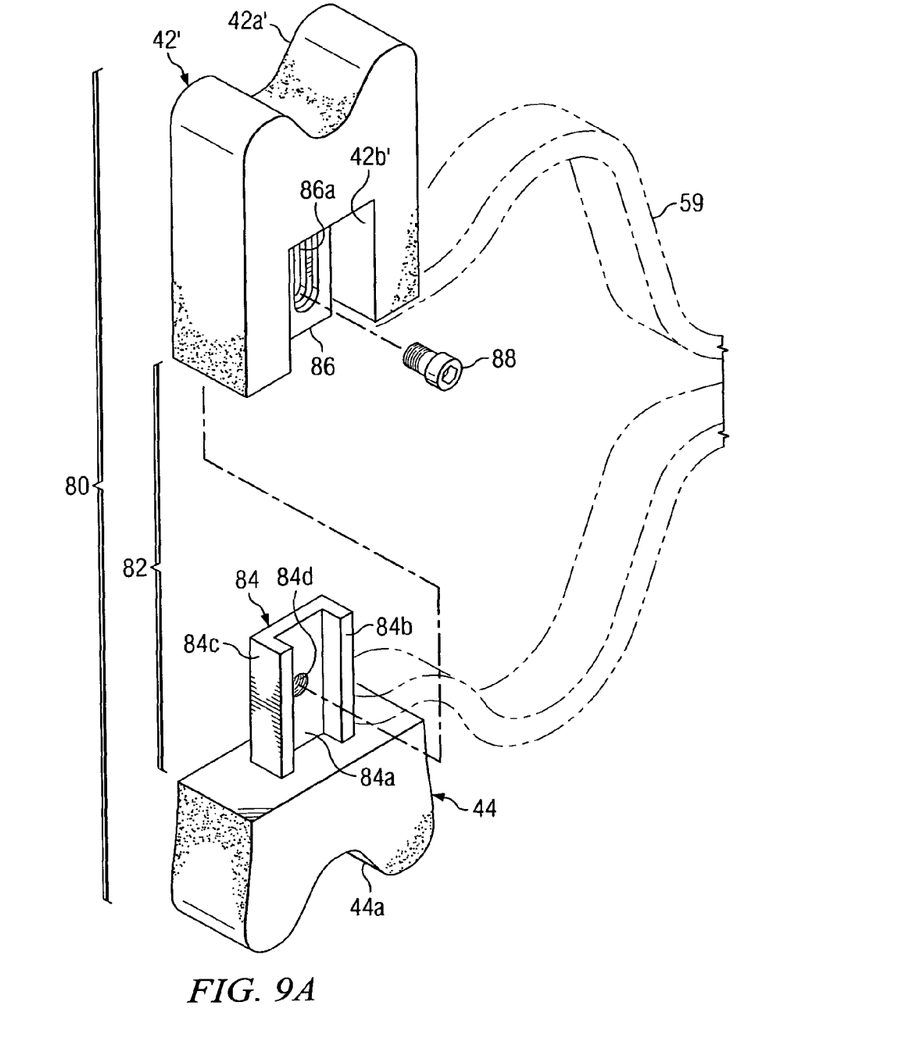
Figure 9B:
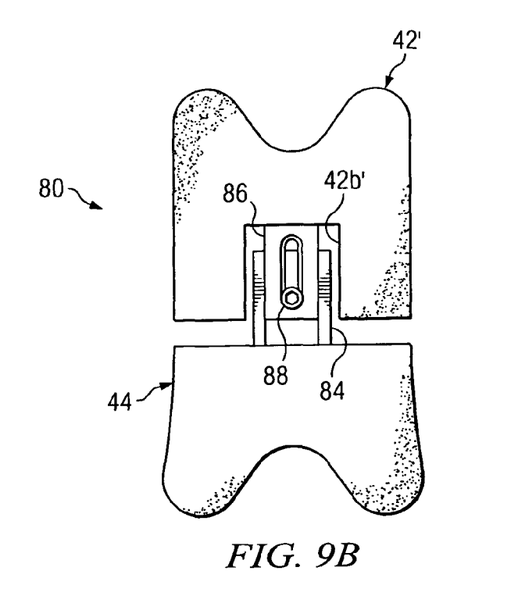
Figure 9C:
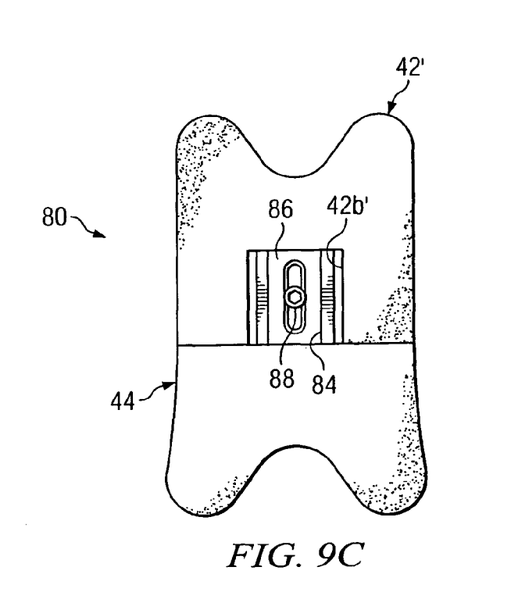

Referring to FIGS. 9A-9C, another embodiment of an intervertebral prosthetic device is shown, in general, by the reference numeral 80 and includes a solid spacer 42' that is similar to the spacer 42 of the previous embodiments. The spacer 42' is fabricated from a relatively soft material and has a curved portion 42a' that receives a process 22 of any of the vertebrae V1-V7, including the vertebrae V4 shown in FIG. 4. According to the embodiment of FIGS. 9A and 9B, a substantially rectangular cut-out 42b' is provided in the lower end of the spacer 42'. The spacer 44 from the previous embodiments is also provided and, since it is well disclosed above, it will not be described in detail.

An adjustable mechanism 82 connects the spacers 42' and 44 while permitting relative axial movement of the members relative to each other. The mechanism 82 consists of a bracket 84 extending from the upper end of the spacer 44, as viewed in the drawings, and connected to the spacer in any conventional manner. The bracket 84 has a substantially U-shaped cross-section that includes a base 84a and two spaced, parallel, legs 84b and 84c extending from, and at right angles to, the base. An internally threaded opening 84d extends through the base 84a.

The mechanism 82 also includes a plate 86 that extends from the base of the cut-out 42b' of the spacer 42' and is connected to the spacer in any conventional manner.

The plate 86 has a rectangular cross section and is sized so as to extend in the area of the bracket 84 defined by the base 84a and the two legs 84b and 84c. An elongated slot 86a is formed through the plate 86.

A set screw 88 is provided that has an externally threaded shank portion that extends through the slot 86a in the plate 86 and threadedly engages the threaded opening 84d in the bracket 84. The screw 88 has a head portion the diameter of which is greater than the width of the slot 86a.

As an initial set-up prior to the surgical procedure, the plate 86 is positioned in the bracket 84, and the screw 88 is extended through the slot 86a and in threaded engagement with the opening 84d of the bracket 84. Then, the screw 88 is tightened only sufficiently to retain the plate 86 in the bracket 84 while permitting relative axial movement of the spacers 42' and 44, while the slot 86a defines the limits of the axial movement.

FIG. 9B shows the spacers 42' and 44 in an assembled, slightly-extended position with the amount of the extension depending, of course, on the distance between the adjacent processes. In this context, and referring to FIG. 4, during the surgical procedure, the device 40 is inserted between the processes 22 of the vertebrae V4 and the vertebrae V5. The surgeon can then manually adjust the mechanism 82, and therefore the spacing between the spacers 42' and 44, intraoperatively in the manner discussed above, until the spinous processes 22 of the vertebrae V4 and V5 extend in the notches 42a' and 44a, of the spacers 42' and 44, respectively, with an optimum fit.

If needed, the distractor 59 shown by the phantom lines in FIG. 9A, and discussed above, can be used to assist in making the above adjustment. The screw 88 is then tightened to the extent that it permits relative axial movement of the spacers 42' and 44 between an extended position, such as that shown in FIG. 9B, and the completely retracted position of FIG. 9C, as necessary, with the length of the slot 86a limiting this movement.

It can be appreciated that after the device 80 has been implanted in the manner discussed above, the device can respond to various movements of the patient that place stress on the vertebral column 10 (FIG. 1) and accommodate these movements by relative movement between the spacers 42' and 44. For example, if the patient bends backwardly, the spacers 42' and 44 would move closer together, and the set screw 88 would permit the relative axial movement. If the patient bends forwardly, then the axial spacing between the spacers 42' and 44 would increase, with the set screw 58 permitting the relative axial movement. In both of the above cases, when the patient returns to a normal position the set screw would permit the spacers 42' and 44 to move back to their original position.

If the above backward movement is extreme, the spacers 42' and 44 could reach a position in which their corresponding ends abut as shown in FIG. 9C. In this position, the end of the spacer 42' that abuts the corresponding end of the spacer 44 would compress slightly since the spacer 42' is fabricated of a relative soft material.

Thus, the device 80 is relatively easy to insert, provides an optimum fit between the processes of two adjacent vertebrae, and is adapted to vary in axial length in response to movements of the patient.

Figure 10A:
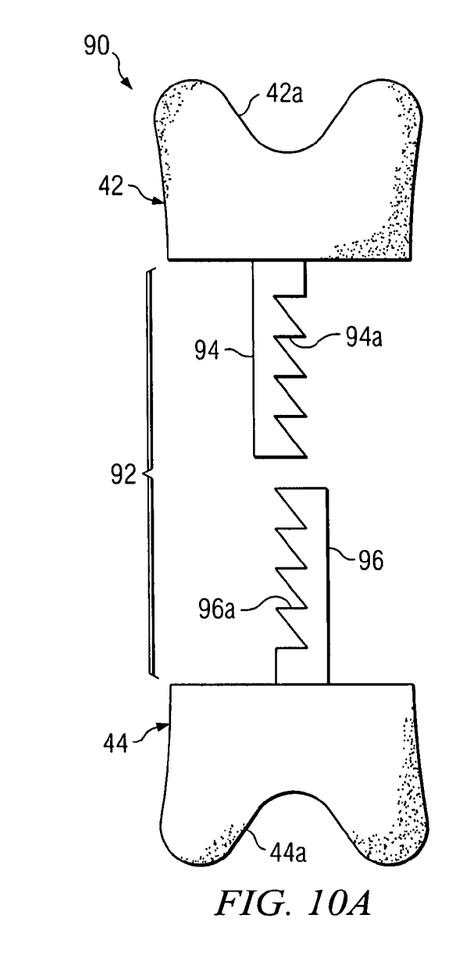
FIGS. 10A-10C are views similar to that of FIG. 7 bit depicting an alternate embodiment.
Figure 10B:
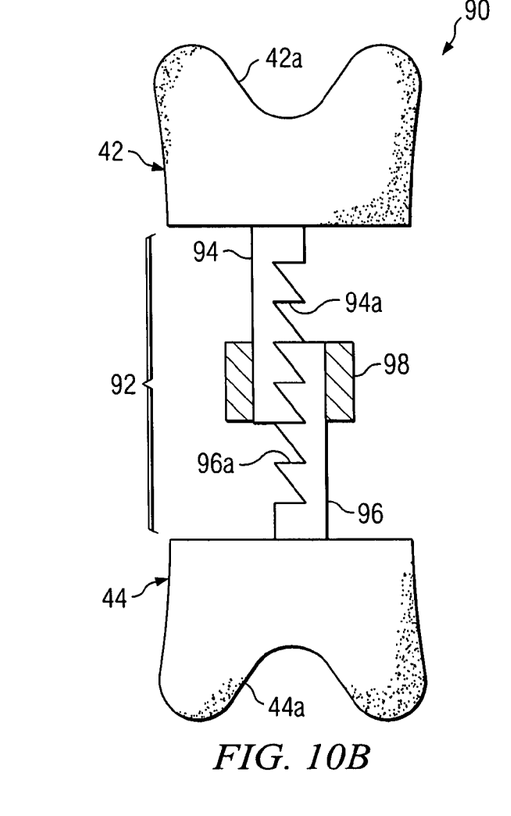
Figure 10C:
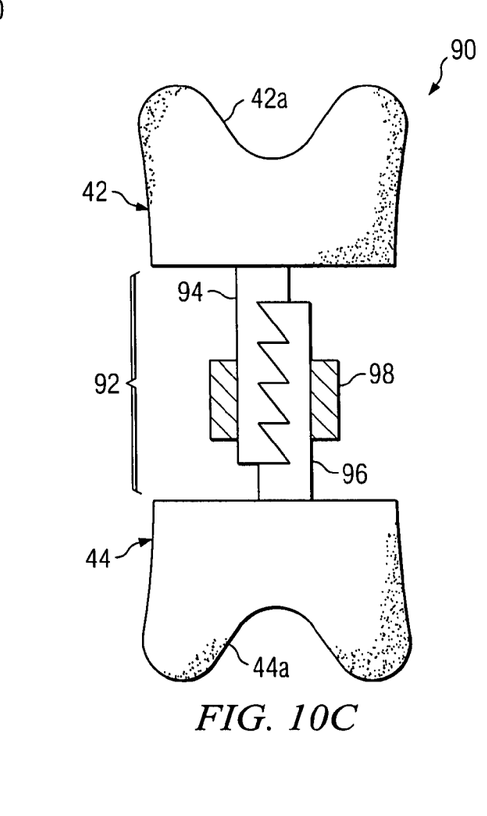

Another embodiment of an intervertebral prosthetic device is referred to, in general, by the reference numeral 90 in FIGS. 10A-10C and is also adapted to be implanted between the spinous processes 22 of the vertebrae V4 and V5.

The device 90 includes the same spacers 42 and 44 of the previous embodiment but utilizes a different connecting mechanism, which is referred to, in general, by the reference numeral 92.

Referring to FIG. 10A, the mechanism 92 includes a plate 94 extending downwardly from the lower end of the spacer 42, as viewed in the drawing, and connected to the spacer in any conventional manner. The inner surface of the plate 94 is provided with a plurality of ratchet teeth 94a each of which has an angled surface extending downwardly from a horizontal surface. A plate 96 extends upwardly from the upper end of the spacer 44 and is connected to the latter spacer in any conventional manner. The inner surface of the plate 96 is provided with a plurality of ratchet teeth 96a each of which has an angled surface extending up from a horizontal surface. The teeth 96a are adapted to mesh with the teeth 94a.

FIG. 10B depicts an operative position of the device 90 in which two of the lower teeth 94a mesh with two of the upper teeth 96a to lock the spacers 42 and 44 in an extended position. FIG. 10C depicts another operative position of the device 90 in which all of the teeth 94a mesh with all of the teeth 96a to lock the spacers 42 and 44 in another extended position. In the positions of FIGS. 10B and 10C, a retainer 98, shown in cross-section, extends around the plates 94 and 96 and retains the plates, and therefore the spacer 42 and 44 in the position shown. It can be appreciated that the spacers 42 and 44 can be locked in relative axial positions other than those discussed above, depending on the number of the teeth 94a and 96a that engage.

The device 90 is inserted between the processes 22 of the vertebrae V4 and the vertebrae V5 in the same manner as the device 40, as shown in FIG. 4 and discussed above. The surgeon can then adjust the longitudinal spacing between the spacers 42 and 44 in the manner described above until the spinous processes 22 of the vertebrae V4 and V5 extend in the notches 42a and 44a, of the spacers 42 and 44, respectively, with an optimum fit. If needed, the distractor 59, shown in the embodiment of FIG. 5, can be used to assist in making the above insertion.

Variations

It is understood that variations may be made in the foregoing without departing from the invention and examples of some variations are as follows:

Any conventional substance that promotes bone growth, such as HA coating, BMP, or the like, can be incorporated in the prosthetic device of one or both of the above embodiments;

The surfaces of the spacers 42, 42', and 44 spacer defining the notches 42a, 42a' and 44b can be treated, such as by providing teeth, ridges, knurling, etc., to better grip the spinous processes and the adapters.

The spacer can be fabricated of a permanently deformable material thus providing a clamping action against the spinous process.

One or both of the spacers 42, 42, and 44 may have through openings formed therein to improve integration of bone growth;

The spacers 42, 42', and 44 and their associated mechanisms 50, 62, 82, and 92 can vary in shape, size, composition, and physical properties;

In the embodiments of FIGS. 5 and 9A-9C, the brackets can be connected to the spacers 42 and 42 and the plates 56 and 86 can be connected to the spacer 44.

One or both of the spacers 42, 42' and 44 may have through openings formed therein to receive tethers for attaching the spacer to a vertebrae or to a spinous process;

In the embodiment of FIGS. 5 and 9A-9C, the bracket 52 can be locked to the plate 56 in manners other than by the set screw 58;

In the embodiment of FIG. 6, only one of the plates 64 or 66 can have teeth formed thereon;

The shape, number, and spacing of the teeth in the embodiments of FIGS. 7, 8, and 10A-10C, as well as the shape of the tabs in FIGS. 7 and 8, can be varied.

The prostheses of the above embodiments can be placed between two vertebrae in the vertebral column other than the ones described above;

Bilateral extrusions, or the like, can be provided on one or more of the devices f the above embodiments to enable a tethering device to be attached;

The prostheses of the above embodiments can be inserted between two vertebrae following a discectomy in which a disc between the adjacent vertebrae is removed, or a corpectomy in which at least one vertebrae is removed.

The prostheses of the above embodiments can be inserted between the facets of adjacent vertebrae, rather than the spinous processes; and The spatial references made above, such as "under", "over", "between", "flexible, soft", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A prosthetic device for insertion between two vertebrae of a vertebral column to stabilize same, the device comprising:

a first spacer having a curved slot in a first end sized to receive and to extend on either side of a spinous process of one of the vertebrae;

a second spacer having a curved slot in a second end sized to receive and to extend on either side of a spinous process of the other of the vertebrae;

a mechanism for connecting the spacers, the mechanism having a variable length extending in a direction that defines a distance between the spacers, the mechanism being configured in a manner to permit sliding relative movement between the spacers so that the distance between the spacers can vary;

wherein the connecting mechanism comprises:

a first flange affixed to the first spacer and extending from the first spacer toward the second spacer;

a second flange affixed to the second spacer and extending from the second spacer toward the first spacer; the second flange having a series of teeth thereon oriented toward the first flange;

a control element disposed between the first and second flanges; the control element engaging at least one of the teeth and operative to control the relative positions of the first and second flanges in said direction.

2. The device of claim 1 wherein the control element comprises a gear surrounded by a retaining collar.

3. The device of claim 1 wherein each tooth comprises a base and a tip extending therefrom, the tip of each tooth being closer to the first flange than the base of the each tooth.

* * * * *